(12) United States Patent
Montenegro

(10) Patent No.: US 8,579,844 B1
(45) Date of Patent: Nov. 12, 2013

(54) TRACTION DEVICE AND ASSOCIATED METHOD FOR INCREASING INTERVERTEBRAL SPACE AND LENGTHENING THE SPINE

(76) Inventor: Nora Montenegro, Chula Vista, CA (US)

( * ) Notice: Subject to any disclaimer, the term of this patent is extended or adjusted under 35 U.S.C. 154(b) by 652 days.

(21) Appl. No.: 12/609,003

(22) Filed: Oct. 29, 2009

Related U.S. Application Data

(60) Provisional application No. 61/197,676, filed on Oct. 29, 2008.

(51) Int. Cl.
*A61F 5/00* (2006.01)

(52) U.S. Cl.
USPC .......... 602/32; 602/33; 602/34; 602/35; 602/36; 602/37; 602/38; 602/39; 602/40; 601/24; 601/25; 601/26; 128/845

(58) Field of Classification Search
USPC ............ 602/32, 33–40; 601/24–26; 128/97.1, 128/845
See application file for complete search history.

(56) References Cited

U.S. PATENT DOCUMENTS

| | | | |
|---|---|---|---|
| 3,768,464 A * | 10/1973 | Greissing | 602/32 |
| 4,650,249 A | 3/1987 | Serber | |
| 4,866,796 A * | 9/1989 | Robinson et al. | 5/607 |
| 4,943,117 A | 7/1990 | Brown | |
| 6,942,297 B2 | 9/2005 | Johnson | |
| 2005/0090771 A1 * | 4/2005 | Miki | 601/99 |

FOREIGN PATENT DOCUMENTS

JP 2002065412 A * 3/2002 ............ A47C 31/11

OTHER PUBLICATIONS

Merriam-Webster Definition of "remote"; http://www.merriam-webster.com/dictionary/remote; accessed Jan. 26, 2013.*

* cited by examiner

*Primary Examiner* — Patricia Bianco
*Assistant Examiner* — Caitlin Carreiro

(57) ABSTRACT

A therapeutic traction device for increasing intervertebral spaces along a cervical spine of a user includes a user interface, a controller, a neck rest section, a crossbar provided with first and second clamps, a curvilinear back pad connected to an anterior side of the crossbar, and a utility box connected to a posterior side of the crossbar. The utility box includes a rectilinear driven rod partially seated within the utility box and statically mated to the neck rest section, and a mechanism for linearly reciprocating the driven rod along a first vertical travel path defined posterior of the back pad such that the neck rest section is synchronously raised and lowered above the crossbar. In this manner, the back pad remains statically mated to the crossbar while the neck rest section is raised and lowered along a second vertical travel path defined anterior of the first vertical travel path.

13 Claims, 9 Drawing Sheets

TRACTION DEVICE AND ASSOCIATED METHOD FOR INCREASING INTERVERTEBRAL SPACE AND LENGTHENING THE SPINE

CROSS REFERENCE TO RELATED APPLICATIONS

This application claims the benefit of U.S. Provisional Application No. 61/197,676, filed Oct. 29, 2008, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to back pain and traction devices and, more particularly, to a home traction device and associated method for providing users with a safe and effective, at-home means of relieving back pain caused by compressed or pinched nerves.

2. Prior Art

In the end, gravity gets us all, one way or another. As we age, the prolonged strain of remaining upright and erect in opposition to the planet's gravitational mass causes parts of out bodies, quite literally, to sag. But the effects of gravity on our upright posture run deeper than the superficial province of the skin, invisibly, our skeletons suffer too.

Over the years, the vertebral discs that cushions our spines take a beating, from the combination of gravity, the gradual loss of elasticity associated with systematic and cellular aging, and the continual pounding we subject ourselves to as we make our way in the world. As a consequence of this, almost everyone, at some point, develops a back problem. Sometimes it's a strain or sprain muscular injury, sometimes a flattened or compressed disc, sometimes a herniated, bulging, or slipped disc, among others.

For many such conditions, the best relief is traction, a gentle but persistent stretching of the spine, accomplished by a device that fastens around the neckline and chin in a contour fashion, and pulls in a steady controlled, non injurious manner, this lengthening the spine and relieving pressure on the vertebral discs. Patients with back problems may receive traction at a physical therapy clinic or a chiropractor's office; but for the most part, a safe and easy to use home traction device has been unavailable.

Accordingly, a need remains for a device in order to overcome the above-noted shortcomings. The present invention satisfies such a need by providing a home traction device that is convenient and easy to use, lightweight yet durable in design, and designed for providing users with a means of relieving pain associated with compressed or pinched nerves, in their own home.

BRIEF SUMMARY OF THE INVENTION

In view of the foregoing background, it is therefore an object of the present invention to provide a therapeutic traction device for increasing intervertebral spaces along a cervical spine of a user. These and other objects, features, and advantages of the invention are provided by a therapeutic traction device including a remote user interface that generates and transmits an input signal upon receiving a user input, a U-shaped neck rest section, and a crossbar disposed subjacent to the neck rest section. Such a crossbar may have first and second clamps formed at axial opposed ends of the crossbar respectively.

The therapeutic traction device further includes a curvilinear back pad removably connected to an anterior side of the crossbar, and a utility box connected to a posterior side of the crossbar. Notably such a utility box includes a rectilinear driven rod partially seated within the utility box and statically mated to the neck rest section, a mechanism for linearly reciprocating the driven rod along a first vertical travel path defined posterior of the back pad such that the neck rest section is synchronously raised and lowered above the crossbar, and a controller communicatively coupled to the user interface and the back pad and the linearly reciprocating means respectively. In this manner, the back pad remains statically mated to the crossbar while the neck rest section is raised and lowered along a second vertical travel path defined anterior of the first vertical travel path. In one embodiment, the back pad may be removably connected to the crossbar with an elastic strap or any other suitable band that will hold the back pad securely to the crossbar.

In one embodiment, the linear reciprocating mechanism may include a motor seated inside the utility box that is communicatively coupled to the controller, a drive pulley driven by the motor, a rotary gear vertically aligned above the drive pulley, and a driven belt attached to the drive pulley and the rotary gear in such a manner that the rotary gear is caused to be automatically rotated along clockwise and counter clockwise directions as the drive pulley rotates along clockwise and counter clockwise directions respectively. In this manner, the driven rod is provided with a plurality of teeth coupled to the rotary gear such that the driven rod is linearly reciprocated along the first vertical travel path as the rotary gear rotates along the clockwise and the counter clockwise directions respectively.

In one embodiment, the controller includes a timer, a processor in communication with the timer, and a memory in communication with the processor. Such a memory preferably includes executable software instructions that generate and transmit a start signal to the motor and thereby toggle the motor to an on mode. Notably, the timer is responsive to the start signal and sends a time signal to the processor when a predetermined period has lapsed after the start signal has been transmitted to the motor. In this manner, upon receiving the time signal, the processor generates and transmits a stop signal to the motor and thereby toggles the motor to an off mode.

The therapeutic fraction device may further include a plurality of support racks anchored to the opposed ends of the crossbar and extending upwardly therefrom, a plurality of shoulder rods removably attached to the support racks, respectively, and a plurality of shoulder pads pivotally mated to the shoulder rods. Such shoulder pads can be independently articulated along mutually exclusive arcuate paths defined subjacent to the neck rest section.

In one embodiment, the back pad may be heated and may further include a plurality of magnets attached to an outer surface thereof.

In one embodiment, the neck rest section may include a chin strap attached thereto.

The present invention may further include a method of utilizing a therapeutic traction device for increasing intervertebral spaces along a cervical spine of a user. Such a method preferably includes the chronological steps of: providing a remote user interface; the user interface generating and transmitting an input signal upon receiving a user input; providing a U-shaped neck rest section; and providing and disposing a crossbar subjacent to the neck rest section wherein the crossbar may have first and second clamps formed at axial opposed ends of the crossbar respectively.

The method may further include the chronological steps of: providing and connecting a curvilinear back pad to an anterior side of the crossbar; providing and connecting a utility box to a posterior side of the crossbar. Such a utility box preferably includes a rectilinear driven rod partially seated within the utility box and statically mated to the neck rest section, a mechanism for linearly reciprocating the driven rod along a first vertical travel path defined posterior of the back pad such that the neck rest section is synchronously raised and lowered above the crossbar, and a controller communicatively coupled to the user interface and the back pad and the linearly reciprocating mechanism respectively.

The method may further include the chronological step of: maintaining the back pad statically mated to the crossbar while raising and lowering the neck rest section along a second vertical travel path defined anterior of the first vertical travel path.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted that the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
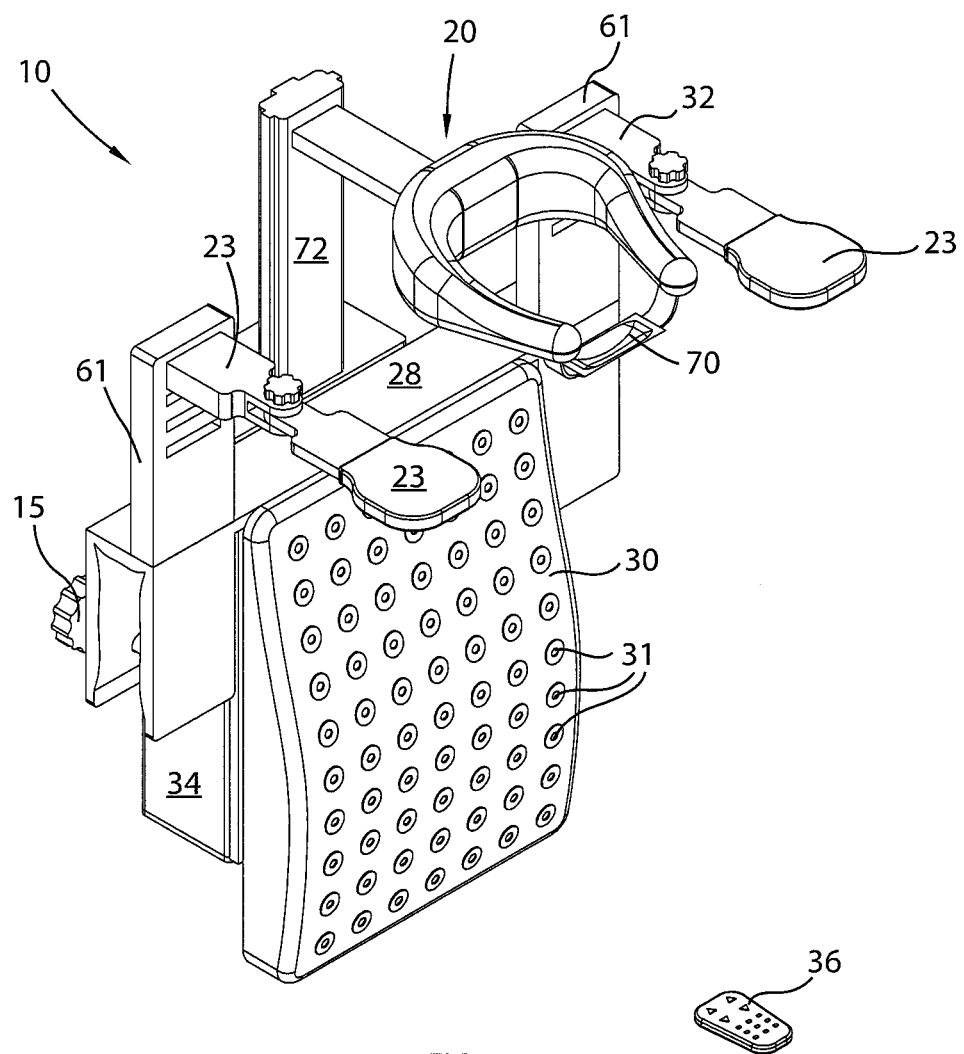
FIG. 1 is a perspective view showing a therapeutic traction device, in accordance with a first embodiment of the present invention.
Figure 2:
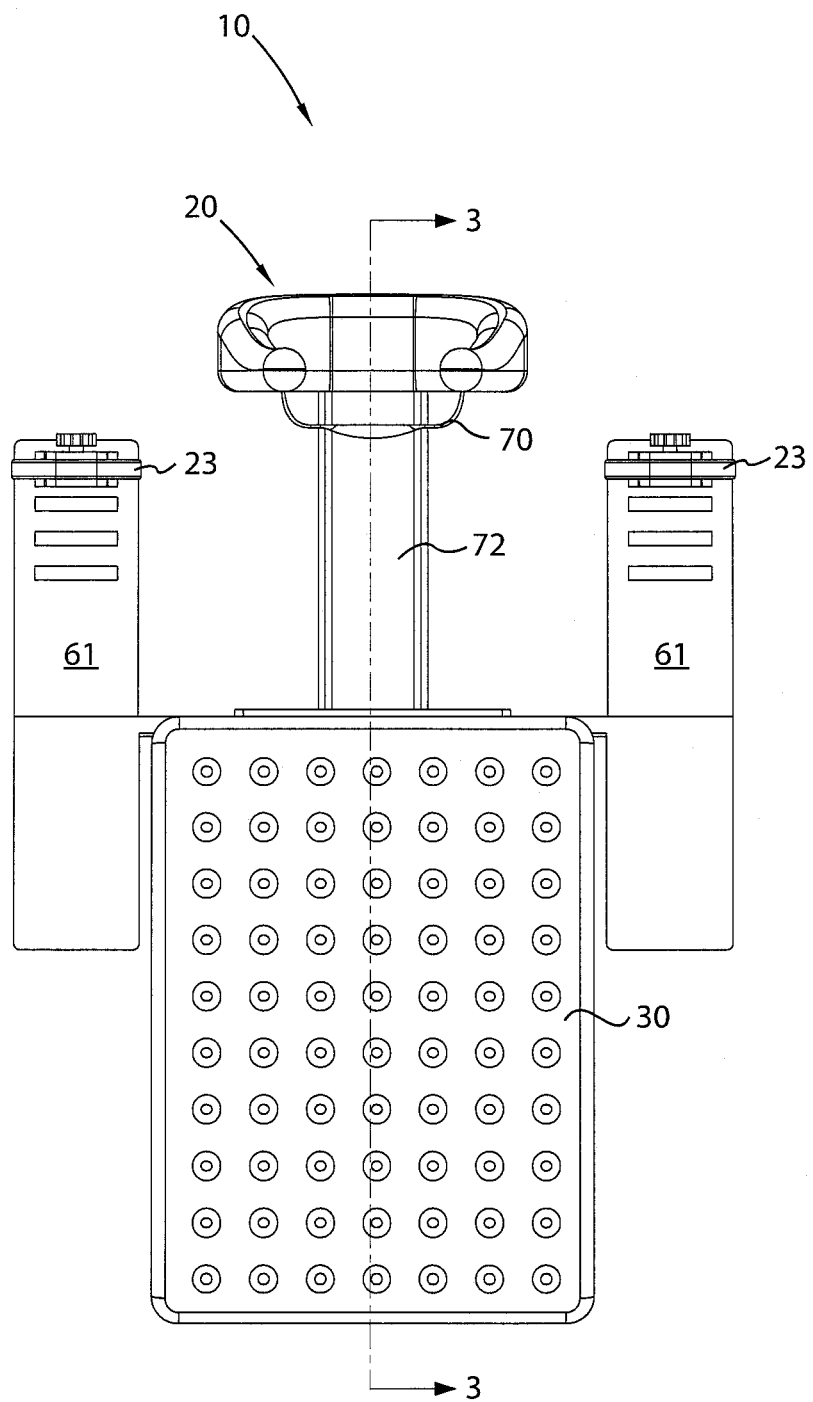
FIG. 2 is a front elevation view of FIG. 1.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The device 10 of this invention is referred to generally in FIGS. 1-12 by the reference numeral 10 and is intended to provide a therapeutic traction device 10 for increasing intervertebral spaces along a cervical spine of a user. It should be understood that the therapeutic traction device 10 may be used to provide relief from pain associated with compressed or bulging intervertebral discs. FIGS. 1-6 and 12 illustrate the first embodiment 10 wherein the linear reciprocating mechanism 50 is motorized. FIGS. 7-11 illustrate the second embodiment 10' wherein the linear reciprocating mechanism 50 is hydraulic.

Referring to FIGS. 1-12, the therapeutic traction device 10 includes a remote user interface 36 that generates and transmits an input signal upon receiving a user input, a U-shaped neck rest section 20, and a crossbar 28 disposed subjacent to the neck rest section 20. Such a crossbar 28 may have first and second clamps 15, 16 formed at axial opposed ends of the crossbar 28, respectively.

The neck rest section 20 preferably is manufactured of formed injection molded thermoplastic and may be padded with polymeric foam. Alternate versions of the back pad 30 are preferably provided wherein one version is heated and the other version is magnetic. The shoulder pads 23 are not linked to the power source 44. The shoulder pads 23 are advantageously used to hold the shoulder down, as an option.

The therapeutic traction device 10 further includes a curvilinear back pad 30 removably connected to an anterior side of the crossbar 28, and a utility box 34 connected to a posterior side of the crossbar 28. Notably, such a utility box 34 includes a rectilinear driven rod 72 partially seated within the utility box 34 and statically mated to the neck rest section 20, a mechanism 50 for linearly reciprocating the driven rod 72 along a first vertical travel path 53 defined posterior of the back pad 30 such that the neck rest section 20 is synchronously raised and lowered above the crossbar 28, and a controller 24 communicatively coupled to the user interface 36 and the back pad 30 and the linearly reciprocating mechanism 50, respectively. In this manner, the back pad 30 remains statically mated to the crossbar 28 while the neck rest section 20 is raised and lowered along a second vertical travel path 54 defined anterior of the first vertical travel path 53. In one embodiment, the back pad 30 may be removably connected to the crossbar 28 with an elastic strap or any other suitable band that will hold the back pad 30 secure to the crossbar 28.

Figure 3:
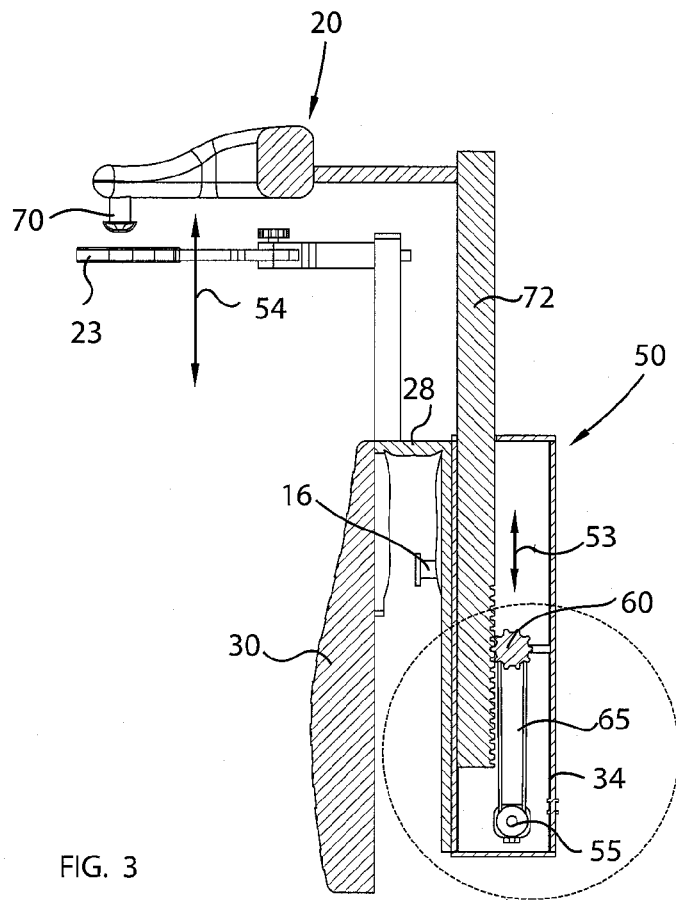
FIG. 3 is cross-sectional view taken along line 3-3 in FIG. 2.
Figure 4:
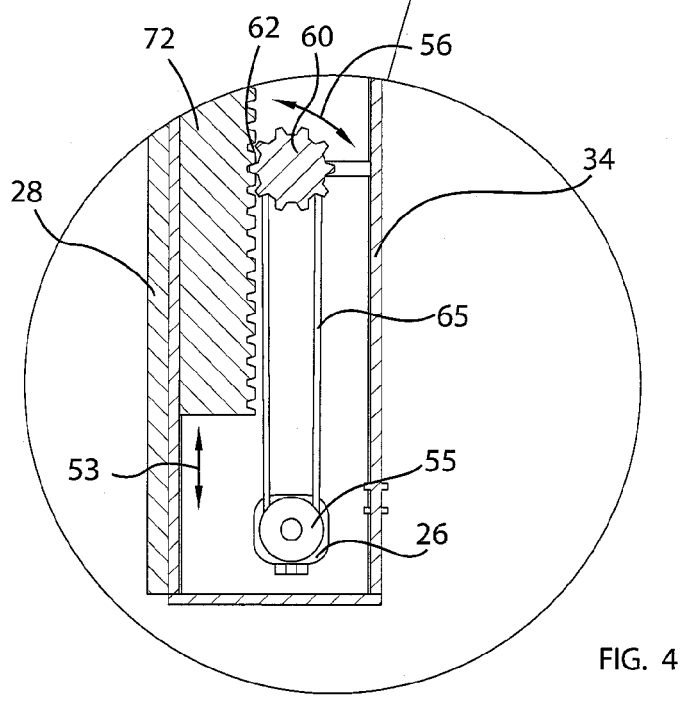
FIG. 4 is an enlarged view showing the motorized linearly reciprocating mechanism, in accordance with the first embodiment.
Figure 5:
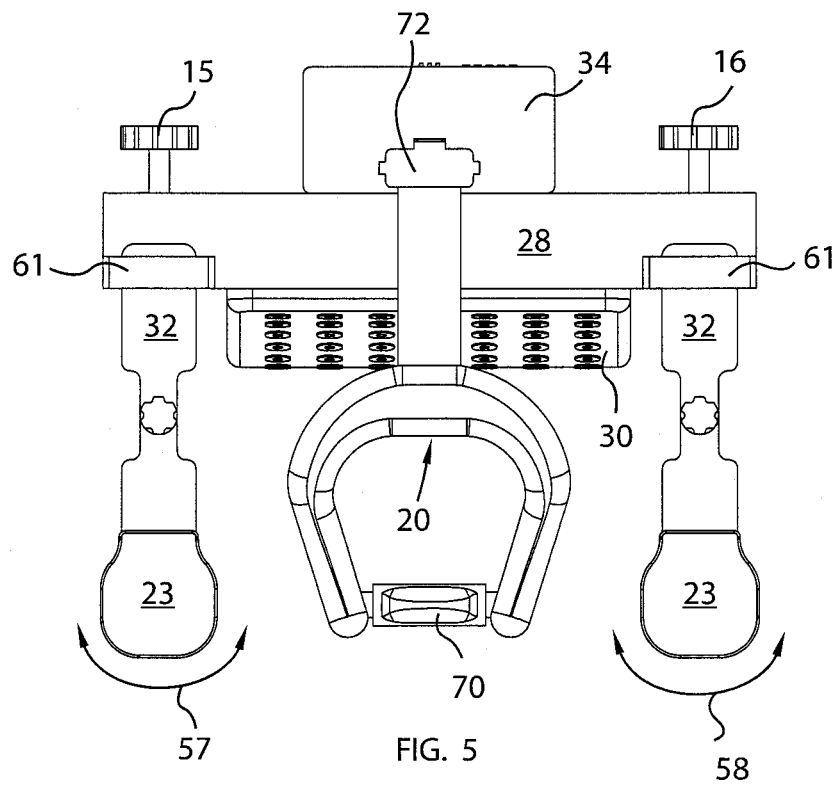
FIG. 5 is a top plan view of FIG. 1.
Figure 6:
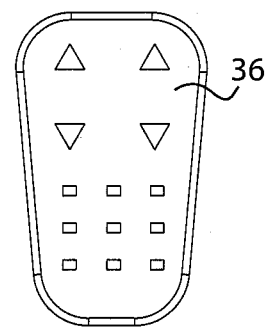
FIG. 6 is a front elevation view of the user interface.
Figure 7:
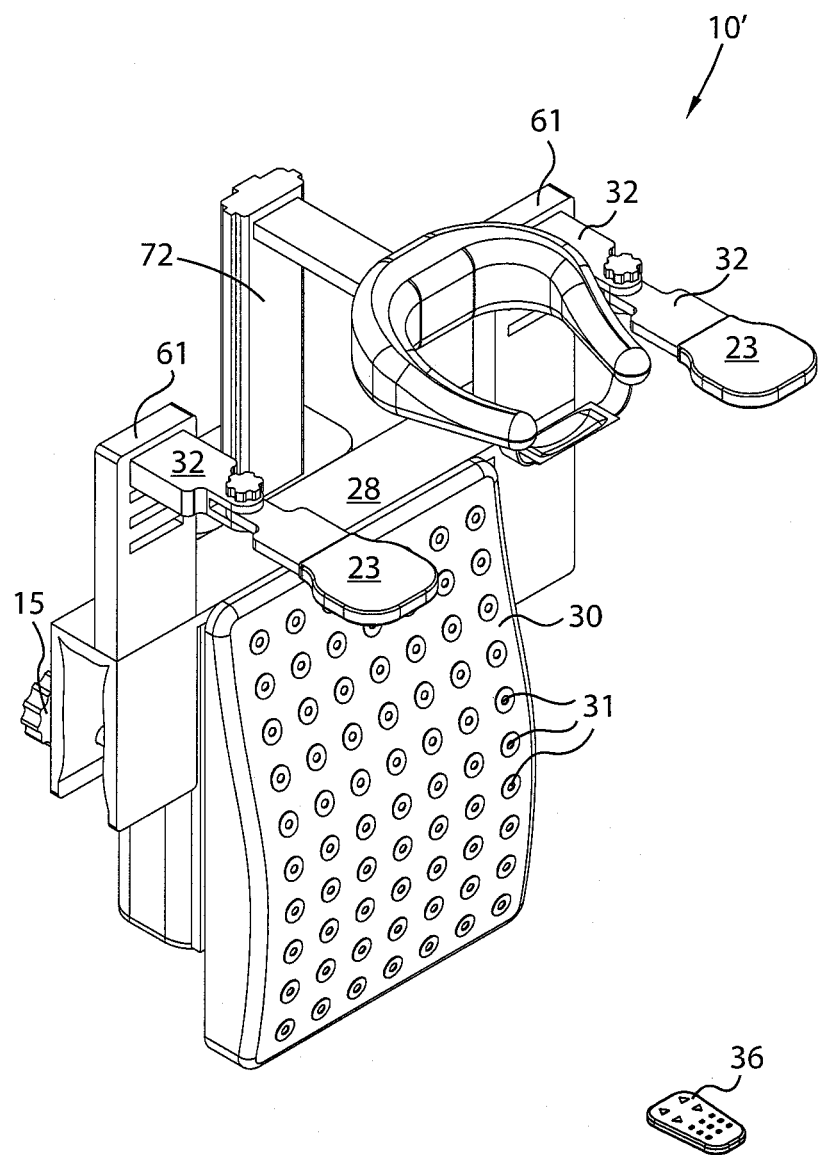
FIG. 7 is a perspective view showing a therapeutic traction device, in accordance with a second embodiment of the present invention.
Figure 8:
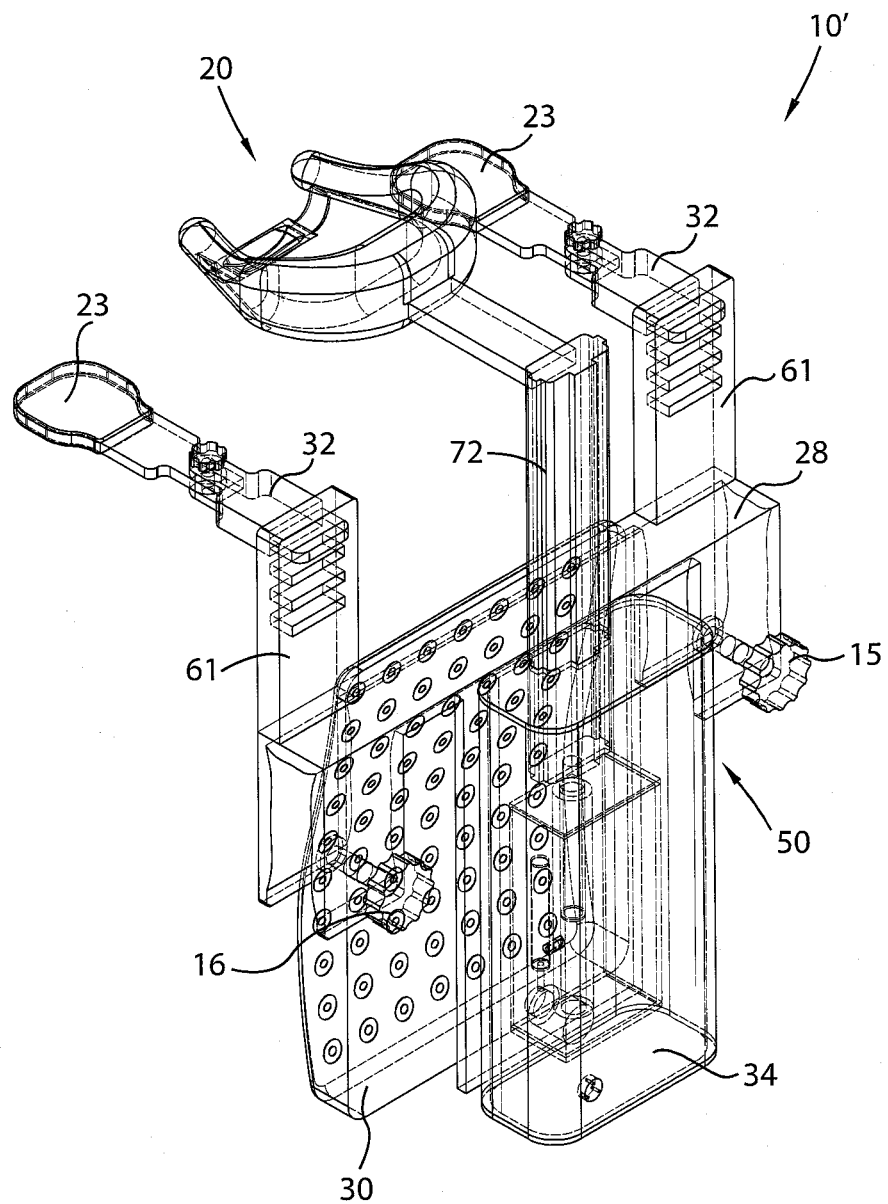
FIG. 8 is a transparent rear perspective view of FIG. 7.
Figure 9:
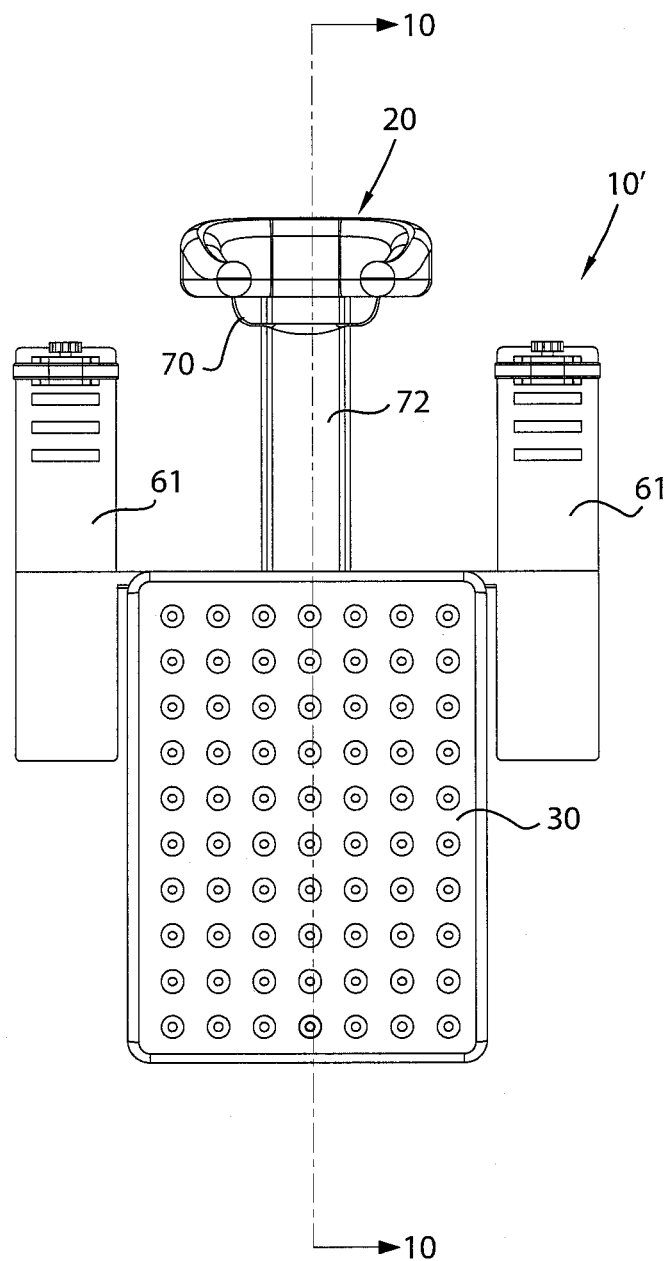
FIG. 9 is front elevation view of FIG. 7.
Figure 10:
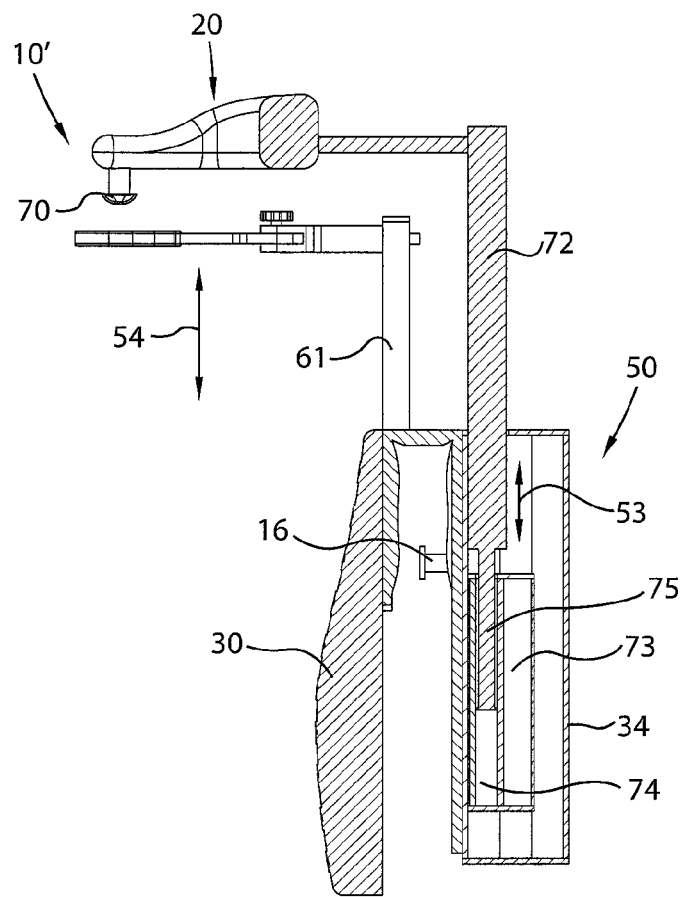
FIG. 10 is a cross-sectional view taken along line 10-10 in FIG. 9, showing the hydraulically actuated linear reciprocating mechanism, in accordance with the second embodiment of the present invention.
Figure 11:
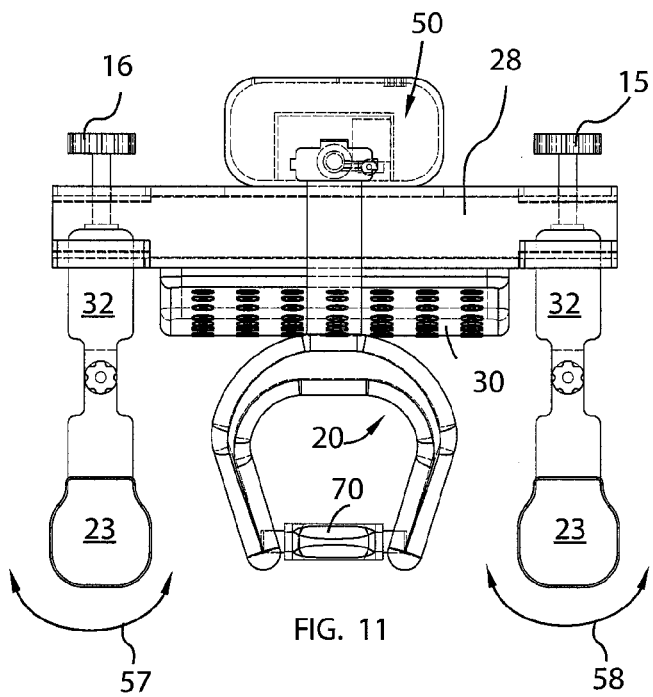
FIG. 11 is a top plan view of the second embodiment shown in FIG. 7.

In one embodiment 10, as perhaps best shown in FIGS. 3 and 4, the linear reciprocating mechanism 50 may include a motor 26 seated inside the utility box 34 that is communicatively coupled to the controller 24, a drive pulley 55 driven by the motor 26, a rotary gear 60 vertically aligned above the drive pulley 55, and a driven belt 65 attached to the drive pulley 55 and the rotary gear 60 in such a manner that the rotary gear 60 is caused to automatically rotate along clockwise and counter clockwise directions 56 as the drive pulley 55 rotates along clockwise and counter clockwise directions 56, respectively. In this manner, the driven rod 72 is provided with a plurality of teeth 62 coupled to the rotary gear 60 such that the driven rod 72 is linearly reciprocated along the first vertical travel path 53 as the rotary gear 60 rotates along the clockwise and counter clockwise directions 56, respectively.

In another embodiment 10', as shown in FIGS. 7-11, the linear reciprocating mechanism 50 is hydraulically actuated wherein a sump 73 includes a quantity of fluid that is transferred into a cylinder 74 and thereby causes the piston 75 to reciprocate the driven rod 72 along the first vertical travel path 53. The transfer of fluid from the sump 73 to cylinder 74 is regulated by controller 24.

Figure 12:
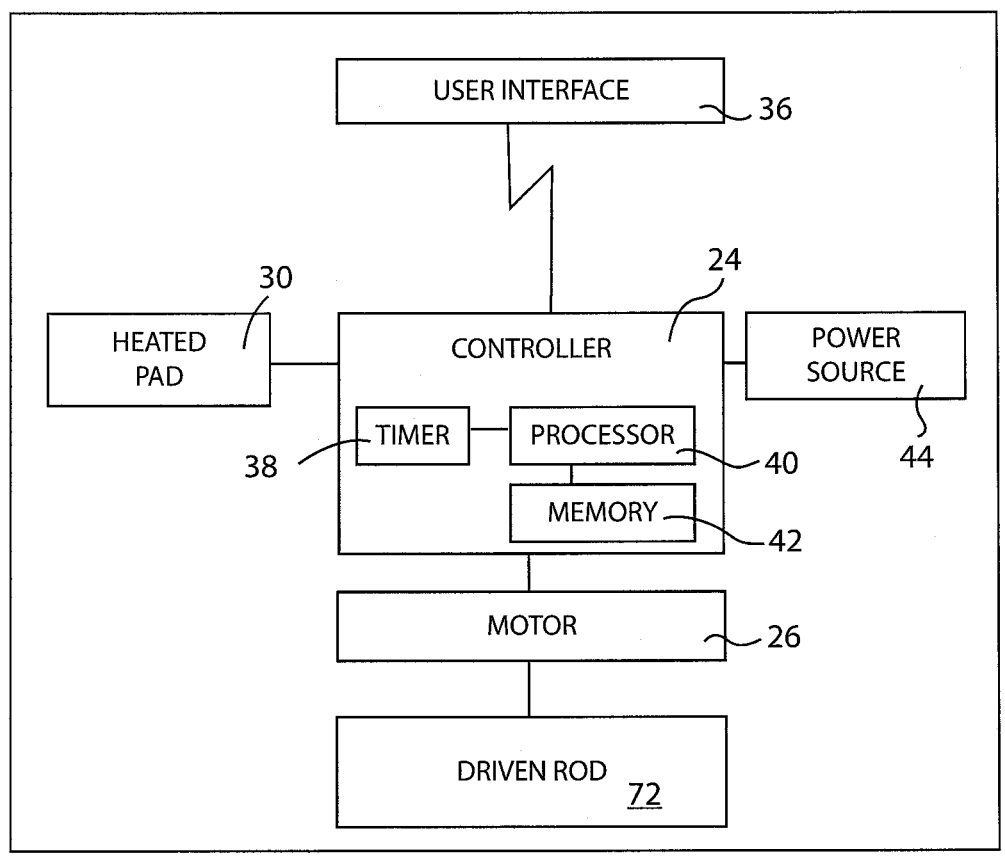
FIG. 12 is a high-level schematic block diagram showing the interrelationship between the major electronic components of first embodiment in FIG. 1.

Referring to FIG. 12, the controller 24 includes a timer 38, a processor 40 in communication with the timer 38, and a memory 42 in communication with the processor 40. Such a memory 42 preferably includes executable software instructions that generate and transmit a start signal to the motor 26 and thereby toggle the motor 26 to an "on" mode. Notably, the timer 38 is responsive to the start signal and sends a time signal to the processor 40 when a predetermined period has lapsed after the start signal has been transmitted to the motor 26. In this manner, upon receiving the time signal, the processor 40 generates and transmits a stop signal to the motor 26 and thereby toggles the motor 26 to an "off" mode. Driven rod 72 automatically lowers to a retracted position when the motor 26 is toggled to the "off" mode.

The user interface 36 may include a variety of stand-alone or shared devices that are capable of generating and transmitting a control signal upon receiving a user input. For example, exemplary user interface devices may include a remote controller employing RF, infra-red, acoustic or cellular technology, as well known in the industry. In alternate embodiments, the user interface may include a handheld computer, a PDA, a cell phone, a keyboard, a mouse, etc. that may be comprised of commercially available hardware and software operating systems, for example. The aforementioned user interfaces are intended to represent a broad category of exemplary user interfaces capable of functioning in accordance with the present invention. Of course, the user interfaces may include other components, peripherals and software applications provided they are compatible and capable of cooperating with remaining devices of the present invention. In addition, the user interfaces may include information, documents, data and files needed to provide functionality and enable performance of methodologies in accordance with an exemplary embodiment of the invention.

Regarding the components of the controller 24, the memory 42 includes programmable software instructions that are executed by the processor. In particular, the programmable software instructions include a plurality of chronological operating steps that define a control logic algorithm for performing the intended functions of the present invention. Such software instructions may be written in a variety of computer program languages such as C++, FORTRAN® and PASCAL®, for example. One skilled in the art understands that such software instructions may contain various Boolean logic processes that perform the intended function of the present invention. Therefore, the specific source or object code of the software program is not intended to be a limiting factor in executing the present invention's intended function.

Functions and process steps described herein may be performed using programmed computer devices and related hardware, peripherals, equipment and networks. When programmed, the computing devices are configured to perform functions and carry out steps in accordance with principles of the invention. Such programming may comprise operating systems, software applications, software modules, scripts, files, data, digital signal processors (DSP), application-specific integrated circuit (ASIC), discrete gate logic, or other hardware, firmware, or any conventional programmable software, collectively referred to herein as a module.

The therapeutic traction device 10 may further include a plurality of support racks 61 anchored to the opposed ends of the crossbar 28. Such support racks 61 extend upwardly from crossbar 28. A plurality of shoulder rods 32 are removably attached to the support racks 61, respectively, and a plurality of shoulder pads 23 are pivotally mated to the shoulder rods 32. Such shoulder pads 23 may be independently articulated along mutually exclusive arcuate paths 57, 58 defined subjacent to the neck rest section 20.

The device 10 is designed to relieve pressure and assist in therapy so that the vertebrae are stretched, allowing the disc some space to revert into place. This will provide relief during the stretch. First, the user may place the device's two vice-style clamps 15, 16 and crossbar 28 on the back of a chair (not shown) and tighten them down. The clamps 15, 16 may be coated in non-slip, non-marring rubber or foam to prevent damage to the chair 11. The crossbar 28 may be light-weight steel or any other such durable material as is obvious to one skilled in the art. The shoulder rods 23 may be coated on the underside with soft polymeric, memory type foam. The heated back pad 30 may be composed of polymeric foam, or any other such material as is obvious to one who is skilled in the art.

Then, the user may sit in the chair and place their neck and head into the neck rest section 20. As the neck rest section 20 is moved up, the user's head moves upward as well. Using the shoulder pads 23 will allow the neck vertebrae to be stretched in the neck area. As for alternate use, without the shoulder pads 23, the entire neck and back areas will be stretched. Thus, shoulder pads 23 prevent the shoulders from being lifted past a certain height and this causes the vertebrae to stretch. The home traction device offers several modes of operation, including a slow and steady upward pull and a phased upward pull with a variety of timed release and pull sequences, as well as several levels of relative force.

In an alternate embodiment, the invention may include back pad 30 that incorporates massage therapy. The back pad 30 could provide a massaging action to the back prior to stretching. This would maximize stretching as the user's muscles will have been warmed up by the massage. During stretching exercises, the massaging action would stop. At the end of the stretching routine the massager could be used to decrease the recovery time for the back pain.

In one embodiment, the back pad 30 may be heated and may further include a plurality of magnets 31 attached to an outer surface thereof. Of course, the magnetic and heatable pads could be used in combination or as stand alone applications.

In one embodiment, the neck rest section 20 may include a chin strap 70 attached thereto. The chin strap 70 secures and prevents the user's head from moving around during stretching procedures.

The present invention may further include a method of utilizing a therapeutic traction device 10 for increasing intervertebral spaces along a cervical spine of a user. Such a method preferably includes the chronological steps of: providing a remote user interface 36; the user interface 36 generating and transmitting an input signal upon receiving a user input; providing a U-shaped neck rest section 20; and providing and disposing a crossbar 28 subjacent to the neck rest section 20 wherein the crossbar 28 may have first and second clamps 15, 16 formed at axial opposed ends of the crossbar 28, respectively. The neck rest section 20 may have a slight upward tilt towards the front to prevent excess pressure on the chin area during stretching procedures.

The method may further include the chronological steps of: providing and connecting a curvilinear back pad 30 to an anterior side of the crossbar 28; providing and connecting a utility box 34 to a posterior side of the crossbar 28. Such a utility box 34 preferably includes a rectilinear driven rod 72 partially seated within the utility box 34 and statically mated to the neck rest section 20, a mechanism 50 for linearly reciprocating the driven rod 72 along a first vertical travel path 53 defined posterior of the back pad 30 such that the neck rest section 20 is synchronously raised and lowered above the crossbar 28, and a controller 24 communicatively coupled to the user interface 36 and the back pad 30 and the linearly reciprocating mechanism 50, respectively.

The method may further include the chronological step of: maintaining the back pad 30 statically mated to the crossbar 28 while raising and lowering the neck rest section 20 along a second vertical travel path 54 defined anterior of the first vertical travel path 53.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention.

In particular, with respect to the above description, it is to be realized that the optimum dimensional relationships for the parts of the present invention may include variations in size, materials, shape, form, function and manner of operation. The assembly and use of the present invention are deemed readily apparent and obvious to one skilled in the art.

What is claimed as new and what is desired to secure by Letters Patent of the United States is:

1. A therapeutic traction device for increasing intervertebral spaces along a cervical spine of a user, said therapeutic traction device comprising:
   a user interface that generates and transmits an input signal upon receiving a user input;
   a neck rest section;
   a crossbar disposed subjacent to said neck rest section, said crossbar having first and second clamps formed at axial opposed ends of said crossbar respectively;
   a back pad connected to an anterior side of said crossbar; and
   a utility box connected to a posterior side of said crossbar, said utility box including
   a rectilinear driven rod partially seated within said utility box and statically mated to said neck rest section,
   means for linearly reciprocating said driven rod along a first vertical travel path defined posterior of said back pad such that said neck rest section is synchronously raised and lowered above said crossbar, and
   a controller communicatively coupled to said user interface and said back pad and said linearly reciprocating means respectively;
   wherein said back pad remains statically mated to said crossbar while said neck rest section is raised and lowered along a second vertical travel path defined anterior of said first vertical travel path.

2. The therapeutic traction device of claim 1, wherein said linear reciprocating means comprises:
   a motor seated inside said utility box and being communicatively coupled to said controller;
   a drive pulley driven by said motor;
   a rotary gear vertically aligned above said drive pulley; and
   a driven belt attached to said drive pulley and said rotary gear in such a manner that said rotary gear is caused to be automatically rotated along clockwise and counter clockwise directions as said drive pulley rotates along clockwise and counter clockwise directions respectively;
   wherein said driven rod is provided with a plurality of teeth coupled to said rotary gear such that said driven rod is linearly reciprocated along said first vertical travel path as said rotary gear rotates along said clockwise and said counter clockwise directions respectively.

3. The therapeutic traction device of claim 2, further comprising:
   a plurality of support racks anchored to said opposed ends of said crossbar and extending upwardly therefrom;
   a plurality of shoulder rods removably attached to said support racks respectively; and
   a plurality of shoulder pads pivotally mated to said shoulder rods and being independently articulated along mutually exclusive arcuate paths defined subjacent to said neck rest section.

4. The therapeutic traction device of claim 1, wherein said back pad comprises: a plurality of magnets attached to an outer surface thereof.

5. The therapeutic traction device of claim 1, wherein said neck rest section comprises:
   a chin strap attached thereto.

6. The therapeutic traction device of claim 1, wherein said controller comprises:
   a timer;
   a processor in communication with said timer; and
   a memory in communication with said processor, said memory including executable software instructions that generate and transmit a start signal to said motor and thereby toggle said motor to an on mode;
   wherein said timer is responsive to said start signal and sends a time signal to said processor when a predetermined period has lapsed after said start signal has been transmitted to said motor;
   wherein, upon receiving said time signal, said processor generates and transmits a stop signal to said motor and thereby toggles said motor to an off mode.

7. A therapeutic traction device for increasing intervertebral spaces along a cervical spine of a user, said therapeutic traction device comprising:
   a remote user interface that generates and transmits an input signal upon receiving a user input;
   a U-shaped neck rest section;

a crossbar disposed subjacent to said neck rest section, said crossbar having first and second clamps formed at axial opposed ends of said crossbar respectively;

a curvilinear back pad connected to an anterior side of said crossbar; and a utility box connected to a posterior side of said crossbar, said utility box including
- a rectilinear driven rod partially seated within said utility box and statically mated to said neck rest section,
- means for linearly reciprocating said driven rod along a first vertical travel path defined posterior of said back pad such that said neck rest section is synchronously raised and lowered above said crossbar, and
- a controller communicatively coupled to said user interface and said back pad and said linearly reciprocating means respectively;

wherein said back pad remains statically mated to said crossbar while said neck rest section is raised and lowered along a second vertical travel path defined anterior of said first vertical travel path.

8. The therapeutic traction device of claim 7, wherein said linear reciprocating means comprises:
- a motor seated inside said utility box and being communicatively coupled to said controller;
- a drive pulley driven by said motor;
- a rotary gear vertically aligned above said drive pulley; and
- a driven belt attached to said drive pulley and said rotary gear in such a manner that said rotary gear is caused to be automatically rotated along clockwise and counter clockwise directions as said drive pulley rotates along clockwise and counter clockwise directions respectively;

wherein said driven rod is provided with a plurality of teeth coupled to said rotary gear such that said driven rod is linearly reciprocated along said first vertical travel path as said rotary gear rotates along said clockwise and said counter clockwise directions respectively.

9. The therapeutic traction device of claim 8, further comprising:
- a plurality of support racks anchored to said opposed ends of said crossbar and extending upwardly therefrom;
- a plurality of shoulder rods removably attached to said support racks respectively; and
- a plurality of shoulder pads pivotally mated to said shoulder rods and being independently articulated along mutually exclusive arcuate paths defined subjacent to said neck rest section.

10. The therapeutic traction device of claim 7, wherein said back pad comprises: a plurality of magnets attached to an outer surface thereof.

11. The therapeutic traction device of claim 7, wherein said neck rest section comprises:
- a chin strap attached thereto.

12. The therapeutic traction device of claim 7, wherein said controller comprises:
- a timer;
- a processor in communication with said timer; and
- a memory in communication with said processor, said memory including executable software instructions that generate and transmit a start signal to said motor and thereby toggle said motor to an on mode;

wherein said timer is responsive to said start signal and sends a time signal to said processor when a predetermined period has lapsed after said start signal has been transmitted to said motor;

wherein, upon receiving said time signal, said processor generates and transmits a stop signal to said motor and thereby toggles said motor to an off mode.

13. A method of utilizing a therapeutic traction device for increasing intervertebral spaces along a cervical spine of a user, said method comprising the chronological steps of:

providing a remote user interface;

said user interface generating and transmitting an input signal upon receiving a user input;

providing a U-shaped neck rest section;

providing and disposing a crossbar subjacent to said neck rest section, said crossbar having first and second clamps formed at axial opposed ends of said crossbar respectively;

providing and connecting a curvilinear back pad to an anterior side of said crossbar;

providing and connecting a utility box to a posterior side of said crossbar, said utility box including a rectilinear driven rod partially seated within said utility box and statically mated to said neck rest section, a mechanism for linearly reciprocating said driven rod along a first vertical travel path defined posterior of said back pad such that said neck rest section is synchronously raised and lowered above said crossbar, and a controller communicatively coupled to said user interface and said back pad and said linearly reciprocating means respectively; and maintaining said back pad statically mated to said crossbar while raising and lowering said neck rest section along a second vertical travel path defined anterior of said first vertical travel path.

* * * * *